United States Patent [19]

Hekker et al.

[11] Patent Number: 4,878,736
[45] Date of Patent: Nov. 7, 1989

[54] CONTROL MEANS AND METHOD FOR OPTICAL INSPECTION SYSTEM

[75] Inventors: Roeland M. T. Hekker; Izhak M. Livny, both of Fairfield, Iowa

[73] Assignee: Global Holonetics Corporation, Fairfield, Iowa

[21] Appl. No.: 137,464

[22] Filed: Dec. 23, 1987

Related U.S. Application Data

[63] Continuation-in-part of Ser. No. 920,513, Oct. 17, 1986.

[51] Int. Cl.$^4$ .................. G02B 27/46; G01N 21/01
[52] U.S. Cl. .................. 350/162.13; 356/237; 364/822
[58] Field of Search .................. 350/162.13; 356/237; 364/822

[56] References Cited

U.S. PATENT DOCUMENTS 3,305,834  2/1967  Cooper et al. .................. 350/162.13
4,695,973  9/1987  Yu .................. 350/162.13

Primary Examiner—Bruce Y. Arnold
Attorney, Agent, or Firm—Bell, Seltzer, Park & Gibson

[57] ABSTRACT

Operation of system components is automatically monitored, controlled and coordinated. The presence at an inspection station of each successive one of the objects to be inspected is automatically detected. Inspection of each such object commences in response to its detection when the monitoring of other system components indicates that they are ready for commencement of the new inspection cycle. The inspection system includes a rotatable disk having mask apertures that move into the line of sight of a light detector. Signals produced by scanning of timing marks upon the disk reflect which one of the plurality of masks is present in the optical path, and determine the intensity of the transform image sampled by said mask means.

29 Claims, 7 Drawing Sheets

CONTROL MEANS AND METHOD FOR OPTICAL INSPECTION SYSTEM

This application is a continuation-in-part of U.S. patent application Ser. No. 920,513, filed Oct. 17, 1986 for TRANSFORM OPTICAL PROCESSING SYSTEM and is related to U.S. patent application Ser. No. 137,417 filed concurrently herewith for METHOD AND APPARATUS FOR OPTICALLY EVALUATING THE CONFORMANCE OF UNKNOWN OBJECTS TO PREDETERMINED CHARACTERISTICS. The disclosures of the aforesaid applications are incorporated herein by reference.

FIELD OF THE INVENTION

This invention relates to an optical object inspection system, and more specifically relates to the control of an optical inspection system in which there is produced a characteristic signature of each object undergoing inspection based upon its transform image. By way of example, the transform image may be a Fourier transform image.

BACKGROUND OF THE INVENTION

Machine vision or inspection systems have become a vital component in integrated manufacturing systems. They can sort, package, and perform defect analysis without human intervention. For instance, by inspecting holes being drilled the system can determine if a drill bit is worn.

Most machine vision systems are based upon digital electronic technology that uses serial or one dimensional processing. An image is captured and stored as a matrix of electrical signals. The image is then preprocessed to enhance edges, improve contrast, and otherwise isolate the object to be recognized. A comparison function compares the enhanced image to one or more stored reference images. These preprocessing and comparison functions are typically performed by standard microelectronic, digital equipment on a bit-by-bit or vector basis. Accordingly, the techniques are typically serial and inherently one dimensional, whereas the images being processed are two dimensional. This dichotomy results in very intensive processing requirements, is particularly difficult for one dimensional digital equipment, and, even with an extraordinary amount of memory capacity and processing capability takes a relatively long time to complete. Digital processing hardware has been enhanced and the software and algorithms have been improved over prior art machine vision systems. However, these improvements have come at the expense of additional system complexity, system costs and programming complexity, and still suffer from the inherent limitations of serial processing.

In some systems, the image to be processed is converted into a Fourier or other transform. The Fourier transform presents information about the image of the object in a very useful, symmetrical pattern which represents the object in terms of its spatial frequencies. However, the calculation of a Fourier transform on a digital computer is extremely intense, and may take a computer as powerful as a Micro Vax II about a minute to complete. Even powerful and expensive state of the art array processors take a full second to merely produce the transform. In modern industrial plants, the production line rates are often a full order of magnitude faster than this.

The computational intensity and time are significantly reduced using parallel processing techniques, such as those available when the real image of the object undergoing inspection is converted to a transform image and optically processed. Following generation of the transform image it is "processed" by quantifying the light from a preselected number of spatial domains or segments of the transform image. These quantities are then electronically processed to provide an abbreviated or composite characteristic signature of the transform image, and thus of the object upon which it is based. In comparison to the time and expenses involved when dealing with entire transform images, the signatures may be rapidly and economically obtained and then evaluated to determine whether the object does or does not conform to preselected standards.

Although possessing the above-noted benefits, an inspection system of the foregoing type must include signature-generating means, in addition to the other system components such as means for generating electrical signal data representative of the appearance of each inspected object, means for receiving such signal data and producing a visual image of each object represented thereby, and means for producing a transform image of the object from the aforesaid visual image. The successful utilization of such an inspection system in association with a high-speed production line or the like, wherein the objects must be inspected quite rapidly, requires rapid and accurate control and synchronization of the operation of the various system components.

SUMMARY OF THE INVENTION

With the foregoing in mind, the present invention provides an improved method and means for controlling the operation of an object inspection system of the type having first imaging means for generating electrical signal data representative of the appearance of each inspected object, second imaging means for receiving the signal data and generating a visual image of the object, third imaging means for receiving and generating a transform image from the visual image of the object, and signature generating means for sampling light from different spatial domains of the transform image and generating electrical signal data representative thereof and collectively defining a characteristic signature of the inspected object. The method and means of the present invention also controls and coordinates the operation of the foregoing system components so as to permit both quite rapid and highly accurate inspection of the objects.

In a preferred embodiment wherein the signature generating means of the inspection system includes movable mask means for obtaining samples of light from different spatial domains of the transform image, the system control means synchronizes the operation of other system components and the movement of the mask means.

The first imaging means of the inspection system may and preferably does include sensing means for sensing the presence of an object at a preselected inspection location, stroboscopic lighting means for illuminating each object at such location, and video camera or similar means for generating electrical signals representative of the appearance of an object present at such location. The control means initiates operation of the stroboscopic lighting means and thereafter ensuing transmission of the desired signal data from the camera means only after it has verified that the object in question is within the field of view of the camera means, and the latter has completed its transmission of signal data representative of the appearance of a preceding object at the inspection location. The control means preferably further delays operation of the light-sampling and other components of the signature generating means of the system until the optical real and transform images of the object undergoing inspection are of an optimal quality.

DESCRIPTION OF THE DRAWINGS

Other features of the invention will be apparent from the following description of an illustrative embodiment thereof, which should be read in conjunction with the accompanying drawings, in which.

DESCRIPTION OF THE PREFERRED EMBODIMENT

Figure 1:
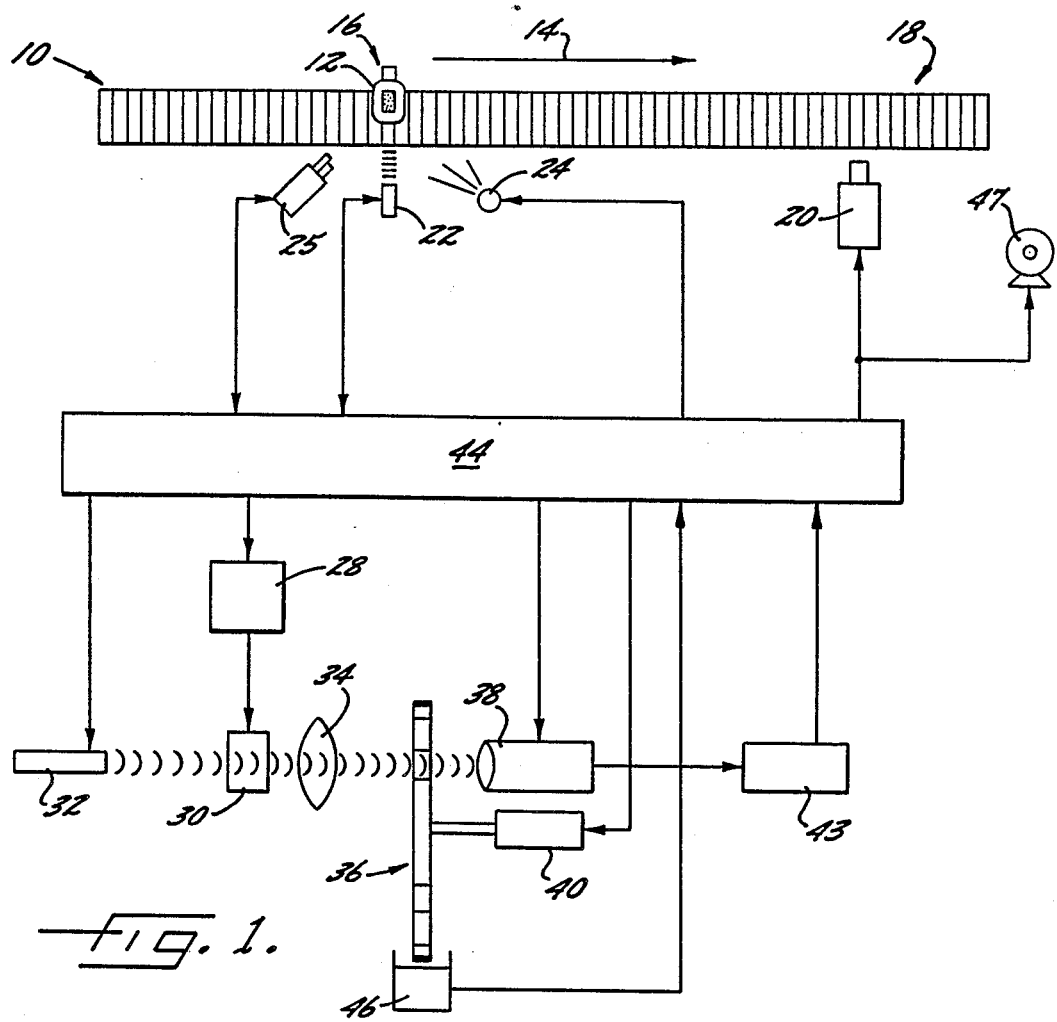
FIG. 1 is a schematic and diagrammatic view of operational and control components of an optical object inspection system in accordance with the invention.

Referring more particularly to the drawings, the numeral 10 in FIG. 1 designates conveyor means for sequentially conducting objects 12, only one of which is shown, in the direction of the arrow 14 along a path of travel extending past an "upstream" object inspection station 16 and a "downstream" object reject station 18. Objects 12 can and normally would be transported by conveyor 10 at a relatively high speed, such as 15 objects-per second, and might be packaged, canned, bottled or other items intended to be of a generally uniform or standardized type. To ensure that objects 12 meet preestablished standards of uniformity, each object is automatically inspected as it reaches inspection station 16. Those objects 12 that fail the inspection are moved laterally from conveyor 10 at reject station 18 by a pusher mechanism 20. The "good" objects that pass the inspection are conducted by conveyor 10 past station 18 to a shipping or other desired location (not shown).

The system for inspecting objects 12 includes first imaging means for producing electrical signal data representative of the appearance of each object arriving at inspection station 16, second imaging means for receiving the aforesaid electrical signal data and producing a visual image of the object, third imaging means for producing a transform image of the object from the aforesaid visual image, signature generating means for sampling light from a limited number of different spatial domains of the transform image and generating therefrom electrical signal data defining a characteristic signature or summary of the transform image and thus of the inspected object, and control means for automatically correlating and controlling operation of the foregoing components.

More specifically with respect to the foregoing components, the first imaging means includes sensing means 22, such as a photoelectric or sonic type object detector, for sensing and signalling the arrival of each object 12 at inspection station 16; stroboscopic lighting means 24 for, when actuated, briefly illuminating the object at the inspection station; and video camera means 26 for capturing the real image of the illuminated object at the inspection station, and producing electrical signal data representative of the real image of the object.

The second imaging means of the inspection system includes frame buffer means 28, and spatial light modulator ("SLM") means 30 which may be and preferably is a liquid crystal display device. Frame buffer 28 receives the signal data essentially in real time as it is generated by camera 26, and retransmits the data to SLM 30 at a predetermined time, causing the SLM to produce a high-quality visual image of the inspected object 12. The frame buffer is typically a fast access random access memory device that stores each line of real image data as it is generated. When all of the real image data has been stored, i.e. the last horizontal trace has been generated and stored, all of the data is transmitted to the spatial light modulator. And, when caused to do so by the control means of the inspection system, frame buffer 28 also causes rapid quenching of the image generated by SLM 30.

The third imaging means of the inspection system includes a laser 32 or other means for producing a coherent beam of light that passes through SLM 30 and defines the optical axis of the system. In passing through the SLM the real image generated by the SLM is impressed on the beam of light. The third imaging means further includes lens means 34 that receives the now modulated light beam carrying the real image of the object 12, and converts that image into a Fourier or other transform image of the inspected object.

Figure 2:
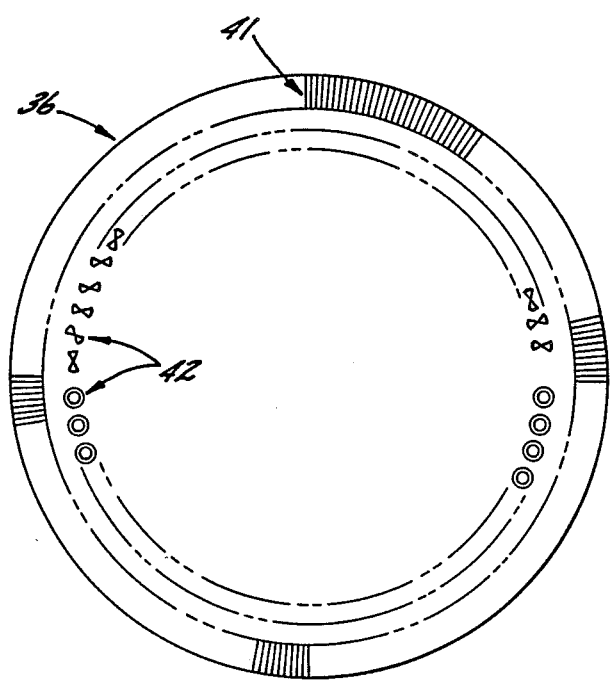
FIG. 2 is an enlarged side elevational view of a rotatable mask component of the system.

The sampling and signature generating means of the apparatus include movable mask means, illustratively in the form of a rotatable disc 36, and light detecting and measuring means such as a photodetector device 38. Disc 36 is adapted to be rotated at a constant speed about its central axis by a servo motor 40, and is also shown in FIG. 2 of the drawings. Disc 36 has a circular array of wedge and ring shaped masks 42 of differing orientations, configurations and/or sizes. Each mask may represent a different spatial domain or segment of the transform image, but together they represent a composite or mosaic of entire image.

As disc 36 undergoes rotation about its central axis, successive ones of the masks 42 move into alignment with the optical path or line of sight between photodetector device 38 and lens means 34. The light transmitted to photodetector device 38 via different ones of disc apertures 42 therefore is from different spatial domains of the Fourier transform image generated by lens 34. The light thus received by photodiode device 38 from a preselected limited number of different spatial domains of the transform image is converted by device 34 into electrical data signals. Such signals are individually representative of the intensity of the light received by detector device 38 from respective ones of the sampled spatial domains of the transform image. Collectively they represent a characteristic signature of the transform image and thus of the object 12 at inspection station 16. By way of example, the disc 36 includes thirty two masks, divided into two sets of sixteen. One set of sixteen includes 16 wedge or "bow tie" shaped masks, and the other set includes 16 ring or donut shaped masks. Each of the wedge shaped masks is $180/16 = 11.25$ arc degrees wide and is oriented at a different arc degree angle in complementary 11.25 arc degree segments. Together the 16 wedge shaped masks form a composite of the entire image area. Similarly, each of the donut shaped masks has a different radius so that together they also form a composite of the entire image area.

The disk also includes timing marks 41 at its perimeter. The timing marks may be masks and may be optically detected using one of several known techniques or sensing means 46 to determine the speed and precise angular orientation of the disc.

The signal data generated by device 38 representing the intensity of the transform image domains defined by each of the masks 42 is processed by conventions signal processing means 43. This may include such things as a current-to-voltage converter, a sample and hold circuit, an analog-to-digital converter, and a buffer means.

Figure 3:
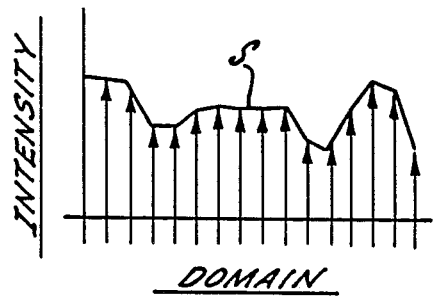
FIG. 3 is a map or graph of the intensity of the transform image in each of sixteen domains, representing the signature of the object being inspected.

The output data from signal processing means 43 is received by a computer, which is also part of the control means 44 of the inspection system. The data received by the computer represents the light intensity for each domain of the transform image. By mapping the intensity for each domain, as shown in FIG. 3, a unique signature line S is generated for each object inspected. The computer contains data, which may be based upon prior analysis of the characteristic signatures of a number of "good" objects previously inspected by the system, that is used to determine from its characteristic signature data whether the object 12 currently undergoing inspection falls within the acceptable limits defining a "good" or "bad" category. In the event of a "bad" category determination, controller 44 directs a control signal to pusher mechanism 20 causing the object 12 in question to be displaced by the pusher mechanism from conveyor 10 when the object reaches reject station 18. Controller 44 may also maintain a record of the number of bad objects detected during a particular time period and actuate an alarm 46 if such number reaches a predetermined limit.

In addition to the foregoing functions, controller 44 automatically controls and coordinates the operation of various of the components of each of the three imaging means and the signature generating means of the inspection system. At the outset of a typical cycle of operation of the inspection system, the arrival of an object 12 at inspection station 16 and within the field of view of camera 26 is detected by detector 22 and reported to controller 44. Controller 44 continuously monitors the operation of camera 26, display device or SLM 28 and photodetector 38. If the condition of the latter components is suitable for commencement of a cycle of operation of the inspection system, the controller 44 initiates the same upon receipt of the signal from detector 22. If one or more of the aforesaid components is not in suitable condition, initiation of the inspection cycle is delayed until it or they are in proper condition.

When the object is in the proper position, controller 44 effects actuation of strobe light 24 and transmission from camera 26 to frame buffer 28 of signal data representative of the real image of the inspected object 12. Such data is received and stored by frame buffer 28, and when the entire real image has been stored it is then transmitted to the liquid crystal SLM 30. The SLM may thereafter be refreshed by the frame buffer for a predetermined time period as necessary and specified by controller 44 and commensurate with the response time of the SLM 30 employed in the inspection system.

The visual image produced by SLM 30, and then impressed upon the light beam generated by laser 32, is converted by lens means 34 into a transform image. The different spatial domains are viewed by photodetector 38 as different ones of the mask apertures 42 of disk 36 move, as the disk rotates, into the optical path of the detector 38.

Constant-speed rotation of disk 36 by its servo motor 40 is initiated by controller 44 when the inspection system is first placed into operation, and i thereafter monitored by the controller. The timing marks 41 present upon the disk 36 are continuously scanned by sensing means 46 (FIG. 1), of a tachometer type, associated with the disk. The output of tachometer 46 continuously produces a signal representative of the uniform rate of rotation of the disk. This signal also permits identification by controller 44 of the instantaneous rotative position of respective ones of the disc apertures 42 relative to the optical path between photodetector 38 and the transform image. The tachometer signal is utilized by the controller 44 to correlate the light intensity signal data generated by photodetector 38 to each successive mask aperture 42 (i.e. transform image spatial domain) of the disk. Such correlation is necessary for proper identification and subsequent comparison, by the computer component of controller 44, of the characteristic signature signal data generated during each inspection cycle with the characteristic signature signal data stored in the computer and relating to "good" objects.

The acceptance of signals from the photodetector 38 during each inspection cycle is delayed until the images generated by devices 30, 34 are in an optimum condition. The duration of the delay depends upon the response time of the particular device 30 employed in the inspection system, as well as possibly other factors. In one particular utilization of the system wherein the inspection cycle time for each object was 66 milliseconds, the transform image was most stable during the last 24 milliseconds of each cycle, and the characteristic signature of the image was obtained during such terminal period. It is of course understood that during such period the generation and/or transmission of signal data by detector 38 is permitted by controller 44 only when successive ones of the mask apertures 42 are aligned with the optical path between the transform image and device 38.

Figure 4:
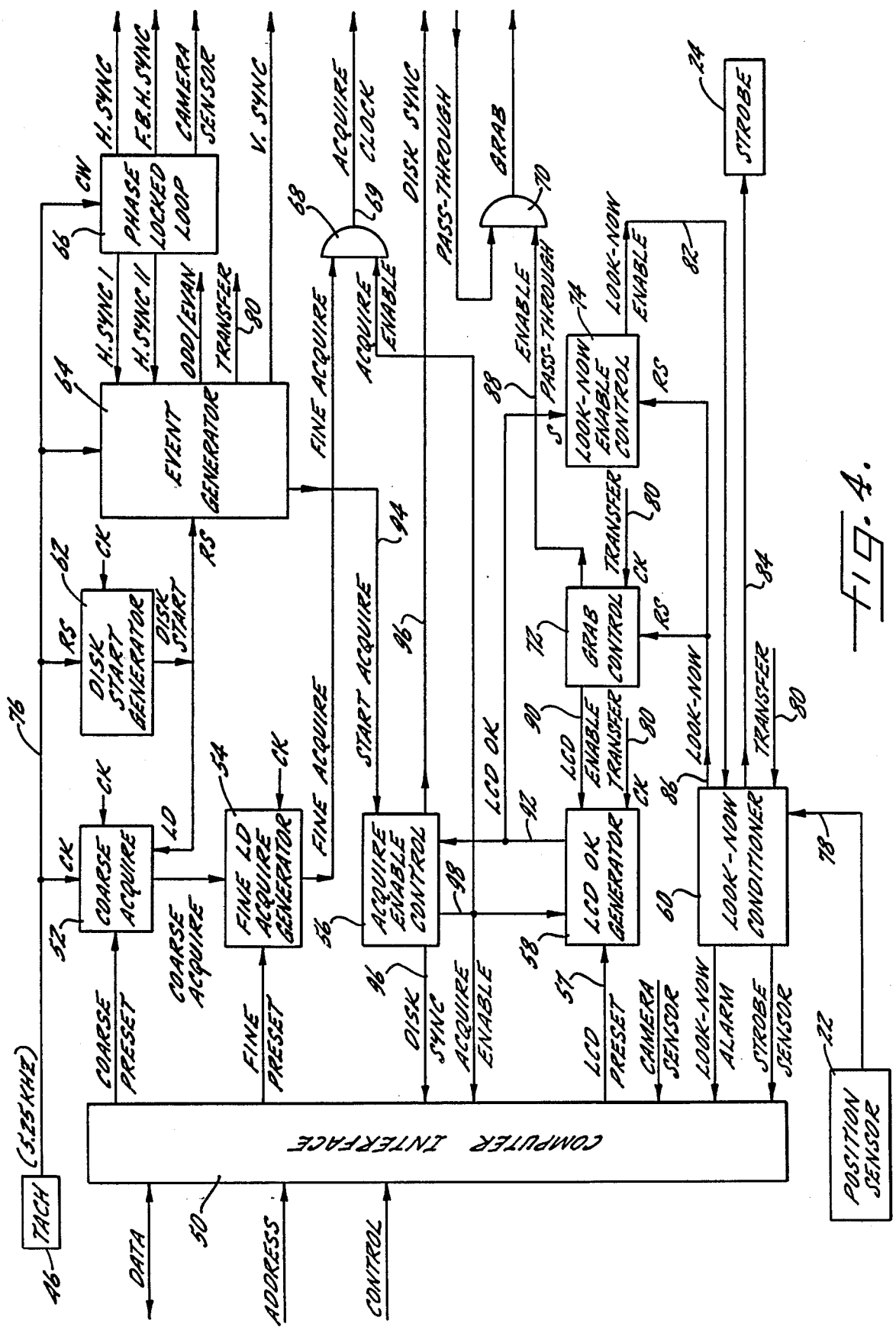
FIG. 4 is a more detailed diagrammatic representation of control components and circuitry of the system.
Figure 5:
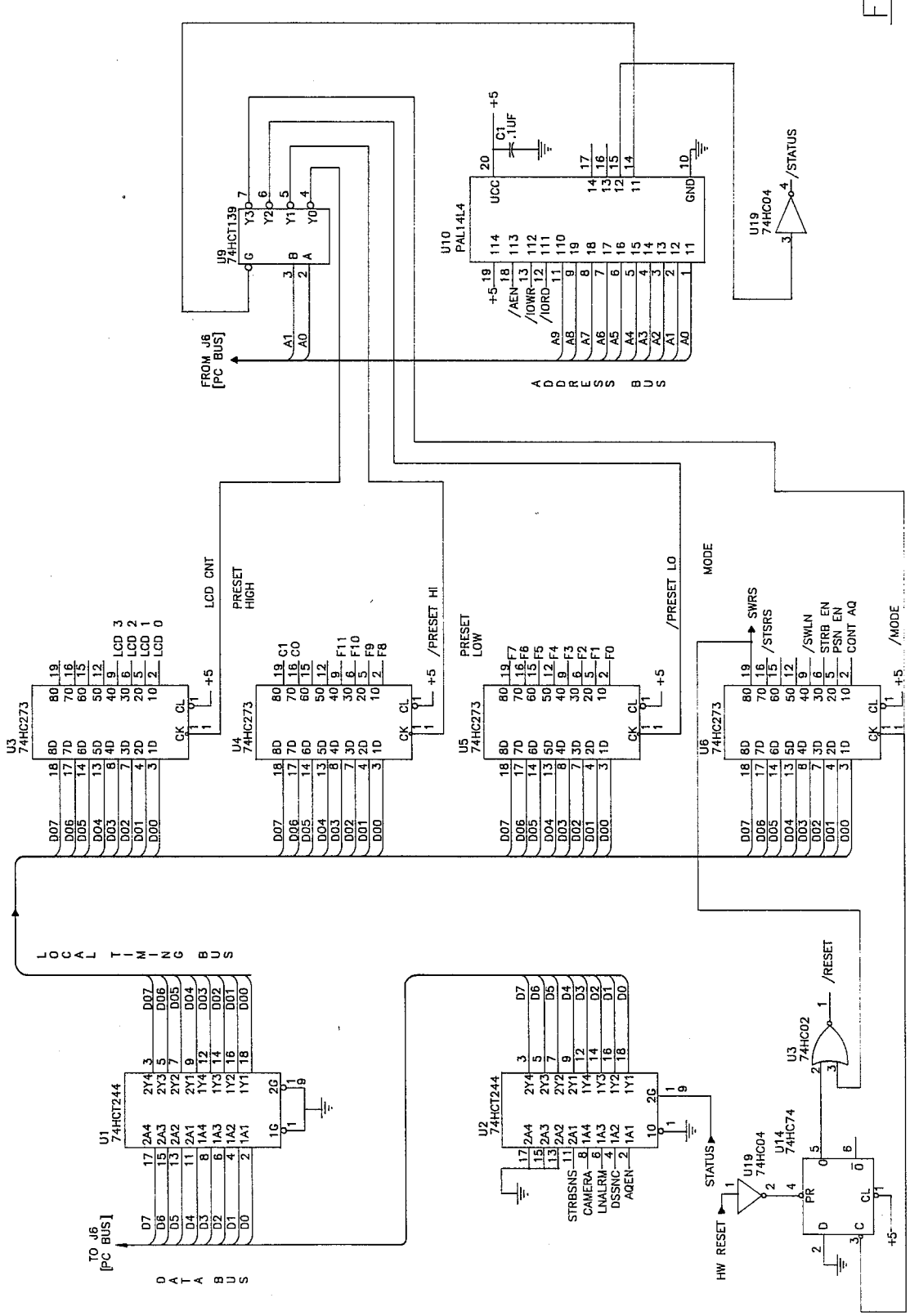
FIGS. 5-9 are circuit diagrams of the control circuitry and related components of the system.
Figure 6:
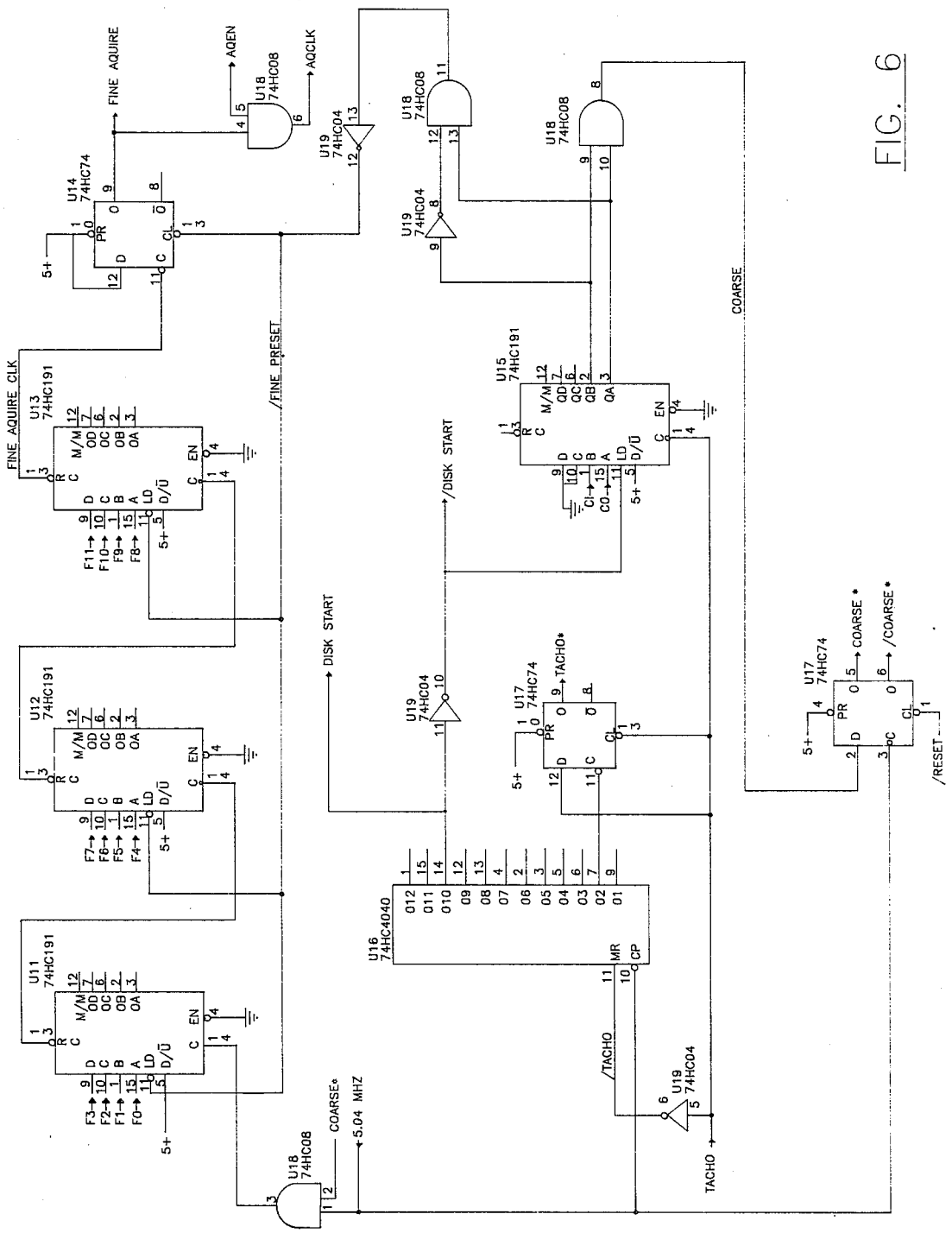
Figure 7:
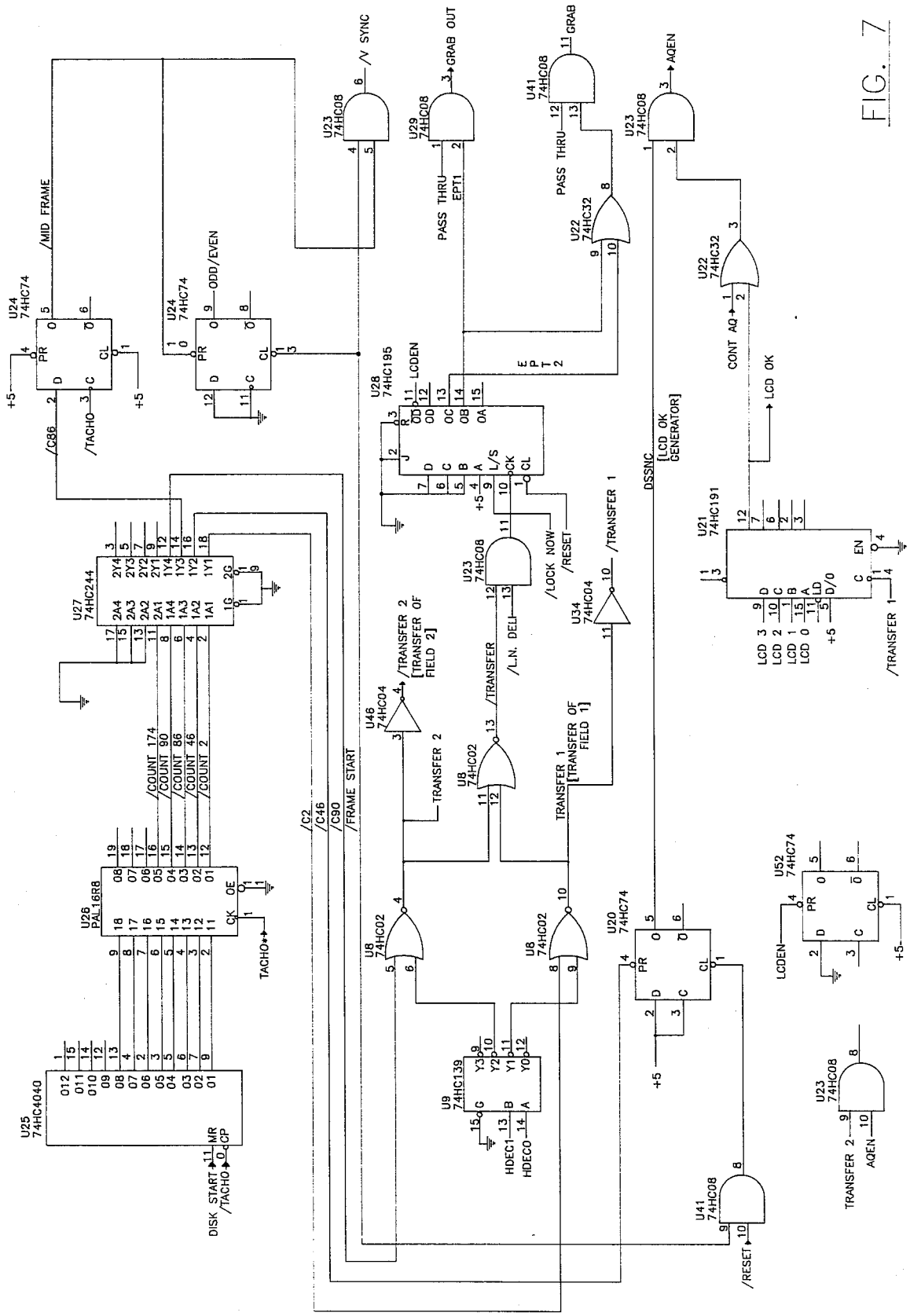
Figure 8:
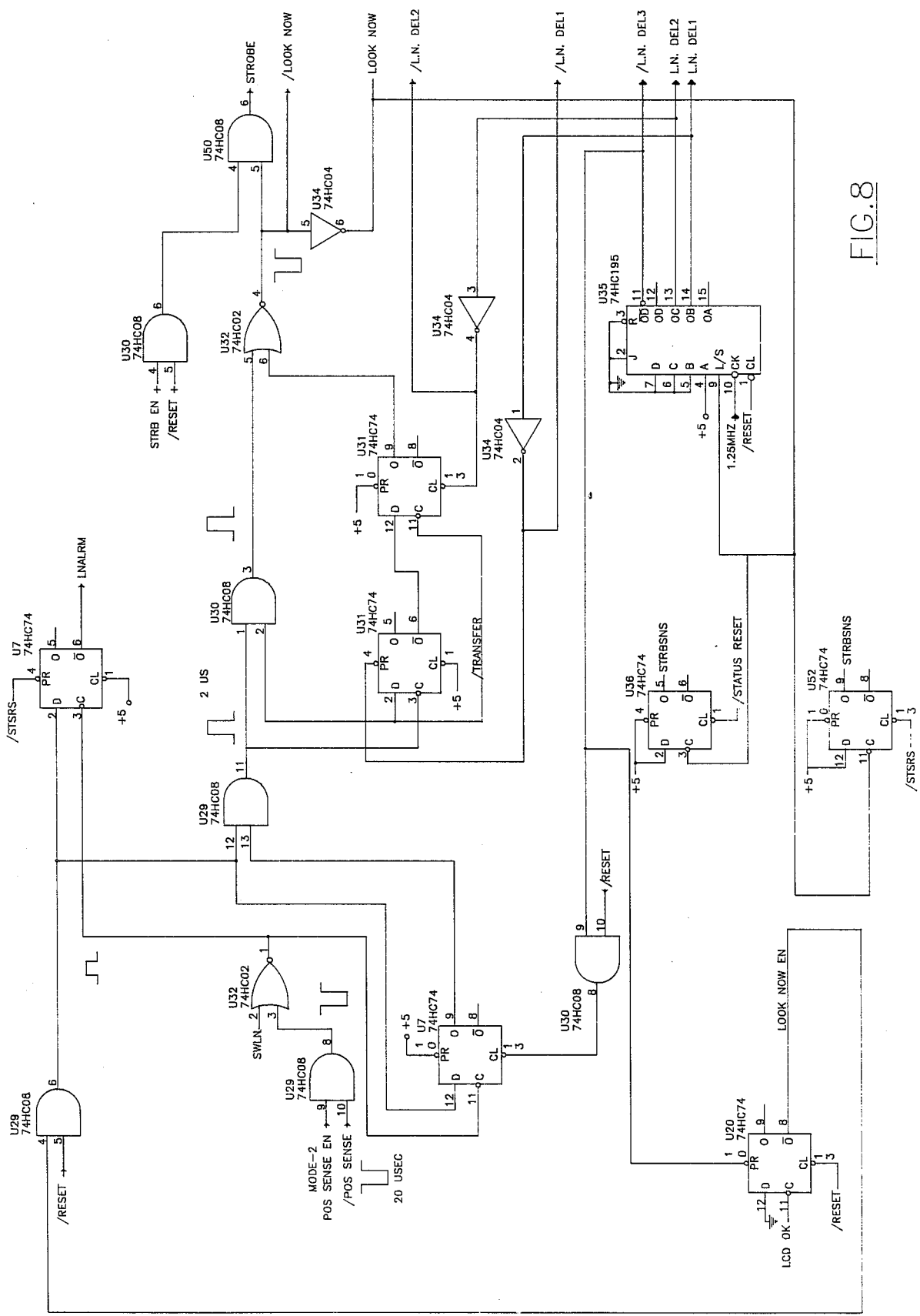
Figure 9:
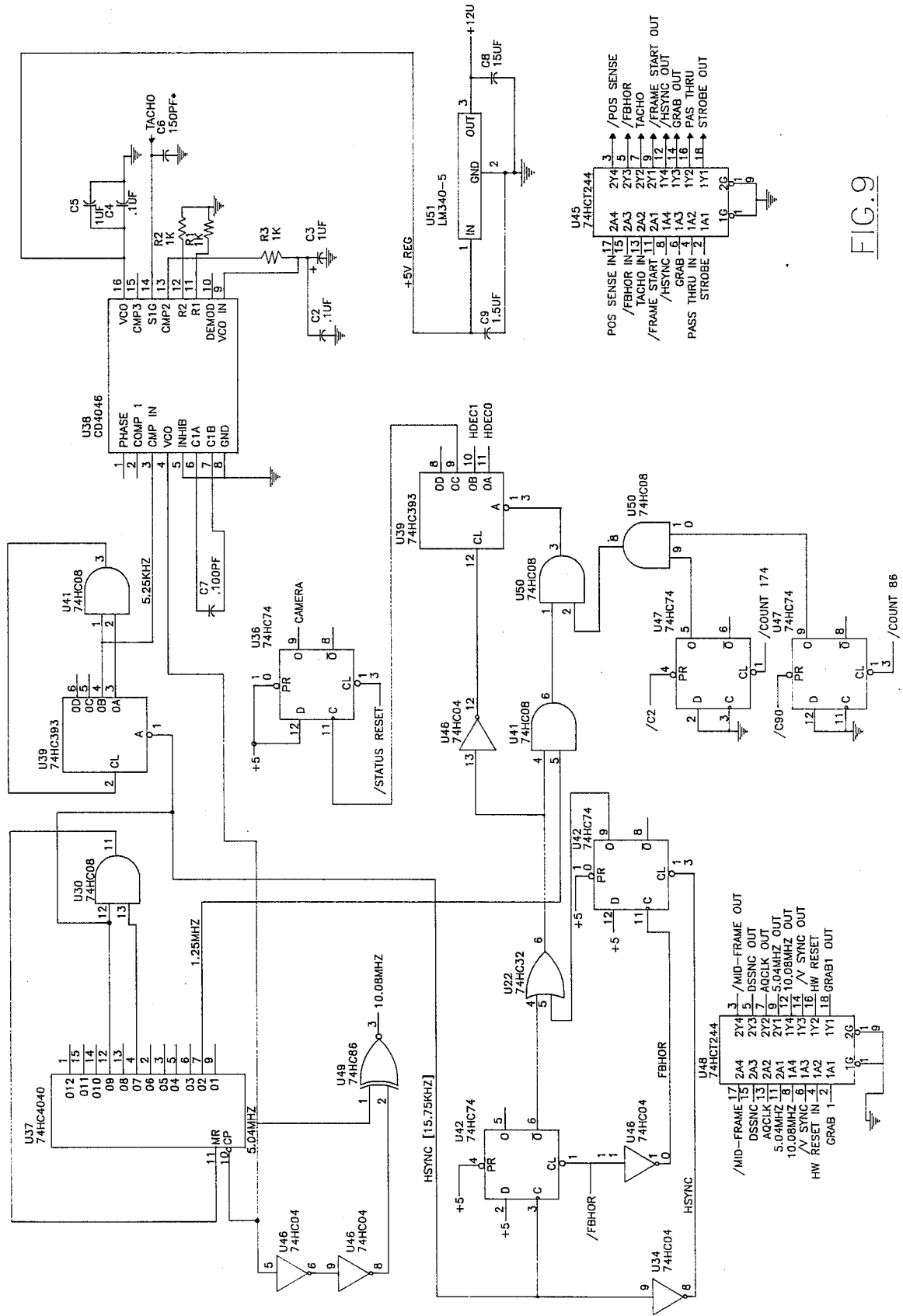

FIG. 4 of the drawings illustrates various of the control components of the system in greater detail. Whenever the inspection system is activated, a timing signal of constant frequency, illustratively 5.25 KHZ, is produced on line 76 by tachometer 46 (FIG. 1) as a result of its scanning of the timing marks 41 (FIG. 2) upon disk 36 as the latter undergoes constant-speed rotation. In response to the line 76 signal a phase locked loop means 66 generates clocking signal data that is utilized to synchronize the operation of other system components with the rotation of disk 36. The signal on line 76 also causes disk start generator 62 to transmit signal data indicative of the commencement of each successive revolution of disk 36. This signal data, in conjunction with that received from line 76 and from phase locked loop means 66, permits precise monitoring by event generator 64 of the instantaneous rotative positions of disk 36 and thus of the disk mask apertures 42.

During operation of the inspection system, the presence at inspection station 16 (FIG. 1) of an object 12 to be inspected causes object sensor or detector 22 (FIG. 1) to transmit a signal to look-now conditioner means 60 via line 78. Conditioner means 60 (and grab control means 72) receive a transfer signal on line 80, from event generator means 64, indicating whether the transfer from camera 26 (FIG. 1) to frame buffer 28 (FIG. 1) of data relating to any previously inspected object has been completed, and thus whether transfer from the camera to the frame buffer of data relating to the object presently at the inspection station can be commenced. Conditioner means 60 also receives a signal on line 82 from look-now enable control means 74. This signal indicates whether liquid crystal display device or SLM 30 has completed or progressed sufficiently toward completion of generation of the image of a preceding object as to permit initiation of a new cycle of system operation with respect to the object currently at the inspection station. Assuming that the signals received by it via lines 80, 82 indicate that conditions are appropriate for institution of a new cycle of operation, conditioner 60 responds to the position sensor signal on line 78 by transmitting a signal via line 84 that actuates strobe light 24, and a signal via line 86 that resets grab control means 72 and look-now enable control means 74. The look now enable control 74 can also be programmed to start the sequence before the previous cycle is complete, consistent with the requirements to capture an entire image. This increases the throughput of the system.

Upon receipt of the reset signal and of a transfer signal on line 80 from event generator 64, grab control means 72 directs an enable pass through signal via line 88 to AND gate 70. Such signal causes gate 70 to emit a grab signal that permits transfer from camera 26 (FIG. 1) to frame buffer 28 (FIG. 1) for one predetermined time period, at the first transfer point occurring after receipt of the enable pass-through signal on line 88. Grab control 72 also transmits an LCD enable signal via line 90 to LCD OK generator 58. This causes the image generated by SLM 30 (FIG. 1) to be periodically refreshed by frame buffer 28 for a predetermined time period, sufficient for the SLM to fully respond, impress the entire image upon the coherent light beam, and to then be quenched. The duration of the predetermined time period will vary depending upon the characteristics of the particular SLM employed in the system, and is governed by an LCD preset signal previously entered into and transmitted from computer interface 50 to generator means 58 via line 57.

The status of the real image produced by SLM 30, and thus also of the transform image produced from the real image, is indicated by signal data produced by LCD OK generator 58 and transmitted on line 92. This same signal is transmitted to acquire enable control means 56.

In response to the signal from LCD OK generator 58 and to a start acquire signal received on line 94 from event generator 64, control means 56 transmits disk synchronization signals (i.e. 30 Hz.) on line 96. It also transmits an acquire enable signal on line 98 to computer 50 and LCD OK generator means 58.

A fine acquire signal from fine acquire generator means 54 and the acquire enable signal on line 98 are received by AND gate 68. The output acquire clock signal of gate 68 on line 69 causes the acquisition of the signal data representative of the intensity of the light transmitted to photodetector device 38 from each of the transform image spatial domains delineated by each of the mask apertures 42 within disk 36. This is done during that particular time period when the image generated by device 30 and lens 34 is most stable and of optimum quality. More specifically, the acquire clock signals of gate 68 result in sampling of the output signal of photodetector 38 at precise time intervals that are synchronized with the passage of respective ones of the mask apertures 42 into alignment with the photodetector, and that are correlated with appropriate ones of the computer addresses adapted to receive the aforesaid signal data.

The high degree of precision required for successful operation in the foregoing regard is realized in part by the coarse and fine acquire generator means 52, 54, which decode and produce (by logic, look-up table, or otherwise) a very fine resolution of the tachometer timing signals received from line 76 and the disk start signals received from disk start generator means 62. The coarse and fine acquire means also receive inputs from computer 50 for determining the exact disk address, within a 100 nanoseconds resolution, for each of the photodetector output signals.

Due to fluctuations in the response time of a liquid crystal SLM, it is important that each wedge or ring sample (as represented by a mask aperture) be taken at the same relative time within the driving or writing cycle of the SLM, as driven by the video camera and frame buffer and related imaging means. This timing may be done using phase lock loop techniques, or by synchronizing the disk motor with the video signals from the camera, synchronizing the video signals from the camera with a home pulse or other signal from the disk without a phase locked looped, or by adding and subtracting video and motor phase differences. These techniques match the sampling sequence to the response time of the SLM, and the fluctuations in the response times within a liquid crystal or other SLM device.

In the circuit diagrams of FIGS. 5-9 of the drawings the illustrated components of the inspection system are identified by their standard commercial designations, which are well known to those skilled in the art. The signal lines also bear names that correspond to those of FIG. 4. Additional description thereof is therefore deemed unnecessary.

While a preferred embodiment of the invention has been specifically shown and described, this was for purposes of illustration only, and not for purposes of limitation, the scope of the invention being in accordance with the following claims.

That which is claimed is:

1. An object inspection system, comprising:
   first imaging means for generating electrical signal data representative of the appearance of each inspected object;
   second imaging means for receiving said signal data and generating a visual image of the object;
   third imaging means for receiving and generating a transform image from said visual image of the object;
   signature generating means for sampling light from different spatial domains of said transform image and generating electrical signal data representative thereof and collectively defining a characteristic signature of said transform image and thus of the inspected object;
   and control means for automatically controlling and coordinating operation of each of said imaging means and said signature generating means.

2. A system as in claim 1, wherein said control means causes said transform image to be generated for a predetermined time period, and said control means causes operation of said signature generating means during a preselected part of said time period when said transform image is of optimal quality.

3. A system as in claim 1, wherein said first imaging means includes object sensing means for sensing the presence at an inspection location of the object to be inspected, stroboscopic lighting means for illuminating the object at said location, and camera means for generating said electrical signal data.

4. A system as in claim 3, wherein said control means monitors the operating condition of said second imaging means, and initiates operation of said lighting means and transmission of said signal data from said camera means when said object sensing means senses the presence of the object at said inspection location and when said second imaging means is in appropriate condition to receive said signal data from said camera means.

5. A system as in claim 4, wherein said second imaging means includes spatial light modulator means, and frame buffer means for receiving said signal data from said camera means and transmitting said signal data to said spatial light modulator means, and wherein said control means causes said signal data to be transmitted from said frame buffer means to said spatial light modulator means for said preselected time period, said spatial light modulator means generating said visual image in response to receipt of said data.

6. A system as in claim 5, wherein said control means causes said frame buffer means to quench said visual image upon expiration of said preselected time period.

7. A system as in claim 1 wherein said third imaging means includes means for directing a coherent beam of light through said second imaging means, impressing upon the coherent light beam the visual image of the object, and lens means for receiving said light beam and visual image impressed thereon.

8. A system as in claim 6, wherein said third imaging means includes means for directing a coherent beam of light through said spatial light modulator means and said visual image is impressed upon said coherent light beam during its passage through said spatial light modulator means, and lens means for receiving said light beam and said visual image impressed thereon and for converting said visual image into said transform image.

9. A system as in claim 1, wherein said signature generating means includes light detecting and measuring means for generating said last-mentioned electrical signal data from light received thereby during operation thereof, movable mask means for transmitting light from different spatial domains of said transform image to said light detecting and measuring means, and wherein said control means coordinates operation of said light detecting and measuring means and movement of said mask means.

10. A system as in claim 9, wherein said mask means is a rotatable disk member having a plurality of mask apertures extending therethrough, and wherein said control means includes means for monitoring the rotative position of said disk means and coordinating the operation of said light detecting and sensing means therewith.

11. An object inspection system, comprising: object sensing means for sensing the presence of an object at a predetermined location, and for generating first signal data indicative thereof;
stroboscopic lighting means for illuminating the object at said location;
camera means for generating second electrical signal data representative of the appearance of the object at said location;
means for generating a coherent beam of light;
imaging means for receiving said second electrical signal data and utilizing the same to produce a visual image of said object, said light beam extending through said visual image and having said visual image impressed thereon;
lens means for generating a transform image of said object from said visual image thereof;
signature generating means for sampling light from different spatial domains of said transform image, and for generating third electrical signal data representative of each domain thereof and collectively defining a characteristic signature of said transform image;
and control means for initiating operation of said stroboscopic lighting means and the transfer of said second-mentioned signal data from said camera means to said imaging means in response to said first signal data generated by said object sensing means.

12. A system as in claim 11, wherein said signature generating means includes light detecting means for generating said third electrical signal data from light received during operation thereof, and rotatable mask means for controlling transmission of light from said spatial domains of said transform image to said light detecting means, and said control means also coordinates operation of said light detecting means with rotation of said mask means.

13. A system as in claim 12, wherein said control means delays operation of said light detecting means until said transform image is in an optimal condition.

14. A system as in claim 12, wherein said control means effects operation of said light detecting means during a time period beginning a preselected time interval after generation of said visual image is commenced.

15. A system as in claim 12, wherein said mask means and said control means include cooperating means for identifying the rotative positions of said mask means.

16. A system as in claim 15, wherein said mask means has a plurality of masks thereon, said masks being sequentially moved by rotation of said mask means into alignment with said light detecting means, and said control means permitting operation of said light detecting means at those times when successive ones of said masks are aligned with said light detecting means.

17. A system as in claim 11, wherein said imaging means includes a liquid crystal display device upon which said visual image is incrementally generated, and further including means associated with said display device for at times refreshing and at other times quenching said visual image.

18. A system as in claim 17, wherein said means associated with said display device includes frame buffer means for acquiring and storing complete frames of said second signal data from said camera means, and said control means also controls the timing of the acquisition by said frame buffer means of each of said frames.

19. A system as in claim 11, wherein said control means also monitors transfer of said second signal data from said camera means.

20. An object inspection system, comprising:
camera means for generating electrical signal data representative of an image of the object;
means for generating a coherent beam of light;

spatial light modulator means for utilizing said electrical signal data to produce a visual image of said object, and for impressing said image upon said coherent beam of light;

transform imaging means for generating a transform image of said object from said first-mentioned image thereof;

signature generating means for sampling light from different spatial domains of said transform image, and for generating electrical signal data representative of each domain thereof and collectively defining a characteristic signature of said transform image;

and control means for coordinating operation of said light modulator means and said signature generating means.

21. A method of object inspection, comprising:

generating electrical signal data representative of the appearance of an object to be inspected;

utilizing the signal data to generate a visual image of the object;

generating a transform image from the visual image of the object;

sampling light from different spatial domains of the transform image and generating electrical signal data representative of different domains thereof and collectively defining a characteristic signature of the transform image and thus of the object;

and automatically controlling and coordinating the steps of generating the visual image of the object sampling light from different spatial domains of the transform image and generating electrical signal data representative thereof.

22. The method of claim 21 wherein the step of automatically controlling and coordinating comprises generating said transform image for a predetermined time period when said transform image is of optimal quality.

23. The method of claim 21 wherein the step of generating electrical signal data representative of the appearance of a object to be inspected comprises sensing the presence at an inspection location of the object to be inspected, illuminating the object at said location using stroboscopic lighting means, and generating electrical signal data from the reflected image of the object.

24. The method of claim 23 wherein the step of automatically controlling and coordinating comprises initiating operation of said lighting means and generating said electrical signal data when said object sensing means senses the presence of the object at said inspection location and when said second imaging means is in appropriate condition to receive said electrical signal data.

25. The method of claim 21 wherein the step of utilizing the signal data to generate a visual image comprises transmitting the signal data to a frame buffer for temporary storage followed by transmission from said frame buffer to a spatial light modulator means for a preselected time period, said spatial light modulator means generating said visual image in response to receipt of said data.

26. The method of claim 21 wherein the step of automatically controlling and coordinating the steps of generating the visual image of the object further comprises quenching the generated visual image of the preceding object.

27. The method of claim 21 wherein the step of utilizing signal data to generate a visual image comprises directing a coherent beam of light through a spatial light modulator means to generate a visual image and define an optical path, and the step of generating a transform image comprises passing said visual image through lens means for converting said visual image into a transform image.

28. The method of claim 27 wherein the step of sampling light from different spatial domains of the transform image comprises rotating a plurality of movable masks means representing different domains of the generated transform image into add out of the optical path, detecting which one of the plurality of masks is present in the optical path, and determining the intensity of the domain of the transform image sampled by said mask means.

29. The method of claim 28 wherein the step of automatic controlling and coordinating further comprises monitoring the rotative position of said disk means and coordinating the operation of said light detecting and sensing means therewith.

* * * * *